US005567610A

United States Patent [19]
Borrebaeck et al.

[11] Patent Number: 5,567,610
[45] Date of Patent: Oct. 22, 1996

[54] METHOD OF PRODUCING HUMAN MONOCLONAL ANTIBODIES AND KIT THEREFOR

[75] Inventors: Carl Borrebaeck; Lena Danielsson; Susanna Möller, all of Lund, Sweden

[73] Assignee: BioInvent International AB, Lund, Sweden

[21] Appl. No.: 323,593

[22] Filed: Oct. 17, 1994

Related U.S. Application Data

[63] Continuation of Ser. No. 888,480, May 22, 1992, abandoned, which is a continuation of Ser. No. 326,664, Mar. 3, 1989, abandoned.

[30] Foreign Application Priority Data

Sep. 4, 1986 [SE] Sweden .................................. 8603711
Feb. 11, 1987 [SE] Sweden .................................. 8603711

[51] Int. Cl.$^6$ .............................. C12N 5/00; C12N 15/00
[52] U.S. Cl. ............................ 435/240.2; 435/172.2
[58] Field of Search .......................... 435/172.3, 172.2, 435/240.2

[56] References Cited

U.S. PATENT DOCUMENTS 4,752,602  6/1988  Lipsky ........................................ 514/19

OTHER PUBLICATIONS

Thiele et al J. Immunology 136(3): 1038, 1986.
Hoffman et al in Principle of *In Vitro* Immunization of Human Blymplocyts, pp. 277–289. Plenun Press 1985.
Borrebaeck, C. A. K. (1986) Tibtech, 49 147.
Borrebaeck, C. A. K. & Moeller, S. A. (1986) J. Immunol. 136, 3710.
Danielsson, L., Moeller S. A. & Borrebaeck, C. A. K. (1986) Immunology 61, 51.
Goldman, R. & Kaplan, A. (1973) Biochim.Biophys. Acta 318, 205.
Ho, M. K., Rand, N. Murray, J., Kato, K. & Rabin, H. (1985) J.Immunol.135,3831.
Hoffman, M. K. & Hirst, J. A. (1985) Principles of in Vitro Immunization of Human B Lymphocytes, pp. 277–289, Plenum Press.
Strike, L. E., Devens, B. H. & Lundak, R. L. (1984)J.Immunol.132, 1798.
Teng, N. N. H., Reyes, G. R., Bieber, M., Fry, K. E., Lam, K. S. & Herbert, J. M.(1985) in Human Hybrodomas and Monoclonal Antibodies (Engleman et al Eds), 71–91, Plenum Press.
Thiele, D. L. & Lipsky, P. E.(1986) J. Immunol. 136, 1038.
Thiele, D. L., Kurosaka, M. & Lipsky, P. E.(1983) J.Immunol. 131, 2282 Chemical Abstracts, vol. 100:84116m, 1984, p. 422.
Medline, NLM Accession No 84034197, J.Immunol. 1983 Nov; 131(5):2282–90.
Chemical Abstracts, vol. 105: 72232m, 1986, Cancer Res.1986, 46(7) 3295–8.
Chemical Abstracts, vol. 96: 117049w, 1982, Dev.Biol.1982, 90(1), 91–8.
Thiele et al, Proc. Natl. Acad. Sci. USA, vol. 82, pp. 2468–2472 (1985).
Thiele et al, The Journal of Immunology, vol. 134, No. 2, pp. 786–793 (1985).

*Primary Examiner*—Suzanne E. Ziska
*Attorney, Agent, or Firm*—Fitzpatrick, Cella, Harper & Scinto

[57] ABSTRACT

A method for the removal of, for in vitro immunization, undesired cells from human lymphocyte containing cell populations is disclosed. For the method, use is made of lysosomotropic agents which are caused to act in vitro on human lymphocyte containing cell populations.

Also disclosed is a method in the in vitro immunization of lymphocytes for use in the production of human monoclonal antibodies. In this method, lysosomotropic agents are caused to act in vitro on human lymphocyte containing cell populations for removing cell populations having a negative effect on the in vitro immunization, whereupon the lymphocytes are in vitro immunized antigen-specifically and immortalized.

Finally, a kit for in vitro immunization of lymphocytes for use in the production of human monoclonal antibodies is disclosed. The kit comprises as active constituents a container containing lymphokines and a container containing lysosomotropic agents.

11 Claims, No Drawings

METHOD OF PRODUCING HUMAN MONOCLONAL ANTIBODIES AND KIT THEREFOR

This application is a continuation-in-part of application Ser. No. 07/888,480, filed May 22, 1992, now abandoned, which is a continuation of application Ser. No. 07/326,664, filed Mar. 3, 1989, now abandoned.

FIELD OF THE INVENTION

The present invention comprises a method for the removal of, for in vitro immunization, undesired cells from cell populations containing human lymphocytes, a method in the in vitro immunization of lymphocytes for use in the production of human monoclonal antibodies, and a kit for in vitro immunization of lymphocytes for use in the production of human monoclonal antibodies.

BACKGROUND OF THE INVENTION

Monoclonal antibodies were introduced in 1975 by Köhler and Milstein. The concept implies fusing immune lymphocytes with a continuous cell line, for example myeloma. A cloning and selection method makes it possible to select and culture cells producing a specific antibody. This cell clone then originates from one original cell ("monoclonal") and produces exactly identical copies of a specific antibody. These monoclonal antibodies have been prepared against a long line of molecules, and this type of antibody has been used and is still being used to an immense extent. Also the commercial development has been considerable, and today a large number of monoclonal antibodies are being marketed, above all for diagnostic purposes.

This development of mouse-monoclonal antibodies (i.e. prepared by means of immune mouse lymphocytes) has not been followed up with human monoclonal antibodies, in spite of the extensive extensive predicted therapeutic use of these antibodies. This is due to the fact that it is extremely difficult to produce, in a practically feasible manner, immune human lymphocytes for immortalization by cell hybridization or transfection. Ethically, patients, volunteers etc. cannot today be immunized with the molecules against which it is desired to produce human monoclonal antibodies, i.e. tumor-associated antigens, bacterial and viral antigens, toxins etc. Up to the present, the procedure was to seek out patients suffering from, for example, infections, tumors etc., thereby to gain access to immune lymphocytes so-called in vivo sensitized lymphocytes). From the practical point of view, this technique is unacceptable.

The development therefore has occurred within so-called in vitro immunization, implying that non-immune human lymphocytes have been immunized in cell culture environment,i thereby to ensure that all types of antigens can be used. These in vitro immunized human lymphocytes are then fused with myeloma or lymphoblastoid cells for continuous production of human monoclonal antibodies. Alternatively, the immune lymphocytes can be transfected with a suitable viral or bacterial genome, thereby to immortalize the cells.

In other words, in vitro immunization is the only technique by which human monoclonal antibodies can be prepared in the future in a practically feasible and ethically acceptable manner. The technique has been developed during a number of years in the murine system, and there exist today, for mouse cells, in vitro immunization methods which function well (Borrebaeck, 1986).

In the human system to which considerable resources have been made available in order to provide for in vitro immunization, there is today nothing which corresponds to the mouse system. This is because the activation requirements for human cells are partly different, and above all because peripheral blood lymphocytes have been used which, possibly, exist in a "deeper" state of rest. Still there are some reports on human in vitro immunization against a few types of haptens, for example bombesin (Ho et al. 1985) and DNP-HSA (Teng et al. 1985), and red corpuscles (Strike et al. 1984; Hoffman & Hirst 1985). These in vitro immunization systems have no lowest common denominator, and different techniques have been used with very different results, frequently with very low yields of specific hybridomas. In addition, there is at present no system at all capable of producing a satisfactory primary immunological response in vitro against thymus dependent antigens. Using different types of T-cell derived lymphokines is one technique which has functioned well in connection with mouse cells (Borrebaeck & Möller 1986) but which alone is not sufficient in the human system. Other attack techniques that have been tried in order to support a human in vitro immunization for the production of human monoclonal antibodies comprise using (1) adjuvant peptides, such as muramyl dipeptide;

(2) monokine supplemented medium;

(3) separation of cell populations with Sepharose/Sephadex, gelatin, plastic, nylon wool adherence, antibody spanning, complement lysis, affinity column;

(4) polyclonal activators, such as endotoxins (LPS), lectins (PHA, PWM, Con A), *Staphylococcus aureus* cells, protein A or G;

(5) special sera, such as ABO, FCS, rabbit serum.

It has now been found that the problem primarily lies int. al. in the removal of cell subpopulations (possibly cytotoxic) capable of suppressing or otherwise preventing the antigen-specific immunological response in vitro.

OBJECT AND CHARACTERISTICS OF THE INVENTION

It therefore is an object of the present invention to provide a method for the removal, for the in vitro immunization, of undesired cells from human lymphocyte containing cell populations, thereby to permit production of a sufficient number of antigen-specifically in vitro activated human lymphocytes which are then further used as a fusion or transfection partner in the production of human monoclonal antibodies. This method of removing undesired subpopulations of cells from human blood, tonsils, lymphatic nodes, spleen cells, bone marrow etc., which up to the present have prohibited a high yield of specifically in vitro immunized human lymphocytes, is characterized by using so-called lysosomotropic agents. These agents possess the specific ability to kill all lysosome containing cells, such as monocytes/macrophages, NK cells and possibly other cells and at present unknown cell subpopulations in as short a time as 30–40 min (Thiele et al, 1983, 1986).

This method thus affords the possibility of adapting in some thirty or forty minutes, and without extensive cell separation experiments (where presently no satisfactory methods are available and, what is more, one does not know exactly which cell one is looking for), the lymphocyte population so that it can be used for in vitro immunization experiments for the production of human monoclonal antibodies. This is possible because the B cells of the lymphocyte population have now been given the possibility of being activated antigen-specifically without any negative effects from lysosomal-positive cells. In this manner, an immune lymphocyte population has been produced which can be used as the only presently available production source of human monoclonal antibodies. This again means that it is possible to start producing human monoclonal antibodies to the same extent as mouse monoclonal antibodies. The immense in vivo potential of human monoclonal antibodies in the treatment of tumors, in locating tumors, poisonings, in preventing transplant rejections etc., can then be exploited.

A further object of the invention is to provide a method in the vitro immunization of lymphocytes for use in the production of human monoclonal antibodies, in which method lysosomotropic agents, derivatives thereof, or substances synthesized on the basis of these agents are caused to act in vitro on human lymphocyte containing cell populations for the removal of cell populations having a negative effect on the in vitro immunization, whereupon the lymphocytes are in vitro immunized antigen-specifically and immortalized. The immortalization may be effected by fusion with murine or human myelomas, lymphoblastoid cell lines, lymphoma cells, or Epstein-Barr viral infection. Furthermore, the immortalization may be effected by transfecting the immune antigen-specific cells with vital, bacterial or mammal genomes.

The lysosomotropic agents that can be utilized for the method are amino acid esters (Goldman & Kaplan 1973) of the type L-leucine methyl ester (Leu-OMe), L-glutamic acid dimethyl ester etc. Also derivatives of lysosomotropic amino acids or peptides based on these derivatives can be used. These agents penetrate the plasma cell membrane and diffuse freely into the lysosomes where they are quickly metabolised to free amino acids. These free and more polar amino acids are unable to diffuse out of the lysosomes as quickly as the methyl esters diffuse in, which entails a rapid increase in the intralysosomal osmotic pressure and a subsequent rupture of these organelles. However, we do not wish to link up the behaviour of the lysosomotropic substances with any specific theory.

The invention also comprises a kit for the removal of, for in vitro immunization, undesired cells from human lymphocyte containing cell populations. The so treated cell populations may then be used for the production of monoclonal antibodies. The kit includes a container which contains lymphokines and a further container which contains lysosomotropic agents, derivatives thereof, or substances synthesized on the basis of these agents. In addition, the kit preferably contains some type of immune response modifying agent, so-called BRM (Biological Response Modifier) and different disposable materials adapted to promote the effect of the reagents on the cell populations, as well as directions for use.

The invention will be described in more detail in the following Examples.

EXAMPLE 1

Human peripheral lymphocytes were purified by means of density centrifugation on a Ficoll gradient. The lymphocytes ($10 \times 10^6$ cells/ml) were treated with 0.45 mg L-leucine methyl ester/ml for 40 min. at 25° C. The medium shall have a low serum level, for which reason RO (RPMI 1640 with 0% fetal calf serum (FCS)) was used. The cells were then washed 2 times in R2–5 (RPMI 1640 with 2–5% FCS), whereupon they were added to the in vitro immunization for production of human monoclonal antibodies. The duration of the in vitro immunization was 6 days, and the immunogen used was 1 µg KLH/ml. The culture also contained the lymphokines TRF, BCDF, IL-½. On day 6, it was tested how many antigen-specific plaque-forming cells had been formed. This number gives a measure of how well the in vitro immunization functions. Cells not treated with Leu-OMe were used for control. The result is shown in Table 1.

TABLE 1

| Cells | Number of plaque-forming cells/ $10^6$ B cells | |
|---|---|---|
| | KLH | Gelatin* |
| Leu—OMe-treated cells** | 1156 | 19 |
| Untreated cells | 7 | 11 |

*Gelatin was used as control antigen in the plaque test.
**In this Example, human peripheral blood lymphocytes were used.

EXAMPLE 2

Human peripheral lymphocytes (PBL) which had been in vitro immunized according to Example 1 with 1 µg KLH/ml for 6 days, were immortalized by fusion with Sp2/0-Ag14 myeloma cells or WIL2-UC729HF2 lymphoblastoid cells by means of polyethylene glycol. After 14–21 days the antigen-specific antibody production of the growing hybrids was tested. The result is shown in Table 2.

TABLE 2

| Cells* | number of hybrids**/ number of tested cells | specific efficiency (%) |
|---|---|---|
| Untreated PBL | 0/96 | 0 |
| Leu—OMe-treated PBL | 17/96 | 18 |

*Human lymphocytes fused with Sp2/0-Ag14. The result with WIL2-UC729HF2 was the same, with absolute figures that were lower by about 30%.
**Number of hybrids which were shown by the test to produce antigen-specific antibodies.

EXAMPLE 3

Human peripheral blood lymphocytes (PBL) were isolated from healthy donors by density centrifugation and further separated into B, T and accessory (A) cells, as described recently (Danielsson, L., Möller, S. A. & Borrebaeck, C.A.K. Immunology 61, 51–55 (1987)). PBL were fractionated into T and non-T cells by rosetting with 2-amino ethyl(isothiouronium bromide)-treated sheep red corpuscles, and the latter cell population was incubated on Petri dishes coated with fibronectin or autologous plasma. Non-adherent cells (B cells) were decanted, and adherent cells (accessory cells) were removed by 10 mM EDTA. The B cells were stimulated with 50 µg *Staphylococcus aureus* Cowan I/ml and irradiated (2000 R) T cells with 10 µg PWM/ml overnight. The accessory cells were stimulated with 5 IU gamma interferon/ml and 10 µm indomethacin. The cell populations were cultured in supplemented RPMI 1640 which contained 10% human AB serum at a cell ratio of 2:1:0.4 (Ti:B:A) for a total of 6 days. The antigenic dose was 1 µg/ml. The culture was supplemented with recombinant IL-2 (5 U/ml) and sPWM-T (25% by vol.), produced as described (Danielsson, L., Möller, S. A. & Borrebaeck C.A.K. Immunology 61, 51–55 (1987)). T cells (10 cells/ml) suspended in serum-free RPMI 1640 were incubated with 2.5 mM freshly prepared Leu-OMe for 40 min. at room temperature. The cells were then washed 3 times in RPMI 1640 which contained 2% human AB serum.

The in vitro immunized cells were tested against the immunogen KLH, an unrelated antigen (gelatin) and against anti-Ig (to give the total number of Ig-secreting cells), using a filter immuno-plaque assay (Danielsson, L., Möller, S. A. & Borrebaeck C.A.K. Immunology 61, 51–55 (1987) and M öller, S. A. & Borrebaeck, C.A.K. J. Immunol. Methods 79, 195–204 (1985)). The plaque number is the mean value of three assays. The results are shown in Table 3.

TABLE 3

Effect of O-methyl-leucine on in vitro immunisation of human peripheral B lymphocytes

| | KLH | Leu—OMe | sPWM—T | IL-2 | A-cell | T-cell | number of PFC*/10⁶ B cells | | |
|---|---|---|---|---|---|---|---|---|---|
| | | | | | | | KLH | gelatin | anti-Ig |
| 1. | − | − | − | − | + | + | 6 | 0 | 1190 |
| 2. | + | − | − | − | + | + | 5 | 0 | 1400 |
| 3. | + | − | + | + | + | + | 112 | 3 | 9500 |
| 4. | − | − | + | + | + | + | 14 | 0 | 7950 |
| 5. | + | + | + | + | + | + | 1021 | 0 | 15360 |
| 6. | − | + | + | + | + | + | 25 | 4 | 13500 |

Thus, if the Leu-OMe sensitive T cell population was removed, and if the remaining T cells were tested together with isolated B and A cells in the same in vitro immunization system, the number of plaque-forming cells increased by a factor 10.

EXAMPLE 4

PBL were isolated from healthy donors, using density centrifugation, and treated with 2.5 mM Leu-OMe, as described in Example 3. The mean number of cells recovered after the Leu-OMe treatment was 70% (n=22). Leu-OMe-treated PBL Were suspended in RPMI 1640 supplemented with 1% by vol. nonessential amino acids, 5 mM L-glutamine, streptomycin (50 μg/ml), penicillin (50 UI/ml), 50 μM 2-mercaptoethanol, and 10% human AB0 serum. The serum was collected from healthy blood donors. Cytokines (IL-2, sPWM-T, gamma-interferon, IL-1, BCDF) and 1 μg KLH/ml were then added to the culture. The final cell concentration was $3.5 \times 10^6$ cells/ml and 4 ml (6 well plate) or 30 ml (75 m² flask) cultures were used. The cells were cultured for 6 days and re-fed on day 3–4 with further medium (20% of original culture volume). sPWM-T contained gamma-interferon (400 U/ml), IL-2 (20 U/ml) and B cell growth and differentiation activities. No significant variation was observed between different batches of sPWM-T when tested in vitro immunizations. The results are shown in the Table below.

TABLE 4

Effect of O-methyl-leucine, IL-2 and gamma-interferon on in vitro immunization of unseparated human peripheral lymphocytes

| | KLH | Leu—OMe | IL-2 | IFN | sPWM-T | number of PFC*/10⁶ B cells** | | |
|---|---|---|---|---|---|---|---|---|
| | | | | | | KLH | gelatin | anti-Ig |
| 1. | + | − | − | − | − | 0 | 0 | 175 |
| 2. | + | − | 5# | 2.5# | + | 12 | 3 | 1530 |
| 3. | − | + | 5 | − | + | 54 | 8 | 26540 |
| 4. | + | + | − | − | + | 1225 | 38 | 33450 |
| 5. | + | + | 1 | − | + | 1150 | 8 | 36780 |
| 6. | + | + | 2.5 | − | + | 1415 | 12 | 34900 |
| 7. | + | + | 5 | − | + | 1445 | 12 | 34000 |
| 8. | + | + | 10 | − | + | 1190 | 0 | 32450 |
| 9. | + | + | 50 | − | + | 945 | 0 | 36800 |
| 10. | + | + | 500 | − | + | 780 | 12 | 18830 |
| 11. | + | + | 5 | 100 | + | 1400 | 16 | 28000 |
| 12. | + | + | 5 | 500 | + | 1340 | 0 | 20400 |
| 13. | + | + | 5 | 2000 | + | 1370 | 0 | 21600 |

*The plaque assay was conducted as described in Example 3. The plaque number is the mean value of three assays.
**The number of B cells was determined by staining to show surface-bound Ig.
U/ml These results show that human peripheral lymphocytes can be directly in vitro immunized with comparable efficiency to separated and Leu-OMe-treated cells, whereby several complicated cell separation steps are eliminated.

EXAMPLE 5

In vitro immunized PBL (1 μg KLH/ml) and malign fusion partner were mixed at a ratio of 2:1 and fused using 30% ($HF_2$) or 45% (NS-1/Sp2/0) polyethylene glycol (molecular weight 1540) with 7% dimethyl sulphoxide (Borrebaeck, C.A.K. Stand. J. Immunol. 18, 9–12 (1983)). The human×human hybrids were resuspended in supplemented RPMI 1640 containing 10% fetal calf serum, 1 mM sodium pyruvate, 132 μg oxaloacetic acid/ml, 100 μM hypoxanthine, 0.4 μM aminopterin, 16 μM thymidine and 15% by vol. HF2-conditioned medium. Mouse myeloma cells were fused and cloned, except that feeder cells were omitted. Both human×human and human×mouse hybrids were plated out in 24 well plates (0.7–1.0×10⁶ cells/well). The hybridomas were screened for production of specific antibodies, using an enzyme immunoassay. To sum up, 96 microtiter wells were each coated with 0.3 μg KLH by allowing the antigen solution to dry in the well. Gelatin (0.1%) was then used in order to block the wells for 30 min. at 37° C. The hybridoma supernatant (100 μl/well) was added to the washed wells and allowed to react for 30 min. at 37° C. Peroxidase-conjugated anti-human Ig antibodies diluted in phosphate-buffered saline solution containing 10% fetal calf serum (100 μl/well) were finally incubated for 60 min., and enzyme substrate (ABTS) was added to develop the immunoassay. The results are shown in the Table below.

TABLE 5

Human × human and human × mouse hybridomas produced by using human peripheral lymphocytes in vitro immunised with KLH

| | Fusion partner | Number of viable hybrids* | Number of specific hybrids* | Specific efficiency (%) |
|---|---|---|---|---|
| 1. | $HF_2$ | 94/96 | 3/94 | 3.2 |
| 2. | $HF_2$ | 96/96 | 5/96 | 5.2 |
| 3. | $HF_2$ | 96/96 | 7/96 | 7.3 |
| 4. | $HF_2$ | 96/96 | 12/96 | 12.5 |
| 5. | $HF_2$ | 96/96 | 14/96 | 14.6 |
| 6. | Sp2/0 | 96/96 | 0/96 | 0 |
| 7. | Sp2/0 | 96/96 | 4/96 | 4.2 |
| 8. | NS-1 | 96/96 | 3/96 | 3.1 |
| 9. | NS-1 | 72/72 | 4/72 | 5.5 |

*Number of growth positive wells/total number of seeded wells
Number of antibody-positive wells/number of growth-positive wells. Antibody-positive value = >4 × the background value (OD 0.120–0.150), as determined by enzyme immunoassay.

Human×human hybridomas secreting antibodies specific to hemocyanin could easily be detected, as will appear from the above results. The specific efficiency (number of wells producing specific antibodies in relation to the number of wells exhibiting cell growth×100) was in the range 3–15%. Human×mouse hybridomas gave a somewhat lower specific efficiency, although the positive values were more consistent (3–5%).

The anti-hemocyanin antibodies were also tested in the enzyme immunoassay against uncoated microtiter wells or wells coated with 0.5 μg bovine serum albumin/well or 0.1% gelatin to ensure that the reactivity was not due to nonspecific binding (Haskard, D. O., Gul, V. & Archer, J. R. J. Immunol. Methods 77, 291–295 (1985)).

EXAMPLE 6

The fusion of in vitro immunized cells and the enzyme immunoassay was performed as described in the legends of Table 5 (Example 5) and Table 6 below. The gelatin blocking step was, however, omitted in the enzyme immunoassay. Digoxin was conjugated to transferrin (Butler, V. P. & Chen. J. P. Proc. Natl. Acad. Sci. (U.S.A) 57, 71–78 (1967) and 1 μg digoxin-transferrin/ml was used for in vitro immunization. The molar ratio of digoxin to transferrin was approximately 5:1. Digoxin conjugated to bovine serum albumin (0.5 μg/well) was used in the enzyme immunoassay. The results are shown in the Table below.

TABLE 6

Human × human and human × mouse hybridomas produced by using human peripheral lymphocytes in vitro immunised with digoxin

| | Fusion partner | Number of viable hybrids* | Number of specific hybrids* | Specific efficiency (%) |
|---|---|---|---|---|
| 1. | $HF_2$ | 118/120 | 2/118 | 1.7 |
| 2. | $HF_2$ | 144/144 | 5/144 | 3.5 |
| 3. | NS-1 | 144/144 | 13/144 | 9.0 |
| 4. | NS-1 | 144/144 | 12/144 | 8.3 |
| 5. | NS-1 | 144/144 | 13/144 | 9.0 |
| 6. | NS-1 | 144/144 | 8/144 | 5.5 |

*Number of growth-positive wells/total number of wells seeded.
Number of antibody-positive wells/number of growth-positive wells. Antibody-positive value = >3–4x (human × human hybridomas) or >4x (human × mouse hybridomas) the background value (OD 0.100–0.110).

As will be evident from the results, human×human hybridomas specific to the immunogenic hapten could be produced, although the specific efficiency was somewhat lower compared to when hemocyanin was used as immunogen. However, no anti-digoxin antibodies were detected if the immunogen was omitted from the culture. Also human× mouse heterohybridomas specific to digoxin were produced, using NS-1 as the maligment fusion partner. The specific efficiency was high, and several hybrids produced antibodies which proved to be strongly positive in the enzyme immunoassay (>7–8×background-OD value). The specificity was tested as described for anti-hemocyanin antibodies (Haskard, D. O., Gul, V. & Archer, J. R. J. Immunol. Methods 77, 291–295 (1985)). The anti-digoxin specific hybridomas were then cloned three times by limiting dilution during a culture period of 10 weeks. After this time, approximately 35% of the original hybridomas still produced antibodies specific to digoxin.

REFERENCES

Borrebaeck, C.A.K. (1986) TIBTECH. 4, 147

Borrebaeck, C.A.K. & Möller, S. A. (1986) J. Immunol. 136, 3710

Danielsson, L., Möller, S. A. & Borrebaeck, C.A.K. (1986) Immunology 61, 51

Goldman, R. & Kaplan, A. (1973) Blochim. Biophys. Acta 318, 205

Ho, M. K., Rand, N. Murray, J., Kato, K. & Rabin, H. (1985) J. Immunol. 135, 3831

Hoffman, M. K. & Hirst, J. A. (1985) in HUMAN HYBRIDOMAS AND MONOCLONAL ANTIBODIES (Engleman, Foung, Larrick & Raubitschek, Eds.), pp. 277–289, Plenum Press Strike, L. E., Devens, B. H. & Lundak, R. L. (1984) J. Immunol. 132, 1798

Teng, N.N.H., Reyes, G. R., Bieber, M., Fry, K. E., Lam, K. S. & Hebert, J. M. (1985) in HUMAN HYBRODOMAS AND MONOCLONAL ANTIBODIES (Engleman et al. Eds.), pp. 71–91, Plenum Press.

Thiele, D. L., Kurosaka, M. & Lipsky, P. E. (1983) J. Immunol. 131, 2282

Thiele, D. L. & Lipsky, P. E. (1986) J. Immunol. 136, 1038

We claim:

1. In an improved method for in vitro immunization of lymphocytes for use in production of human monoclonal antibodies, the improvement comprising:

exposing human peripheral blood lymphocytes to a lysomotrophic agent selected from the group consisting of L-leucine-O-methyl ester, L-glutamic acid dimethyl ester and L-leucyl-L-leucine-O-methyl ester to produce treated human lymphocytes; and exposing said treated human lymphocytes to an antigen to activate lymphocytes wherein said treated, activated lymphocytes produce antibody which specifically binds said antigen.

2. The method of claim 1, wherein said lysosomotropic agent is L-leucine-O-methyl ester.

3. The method of claim 1, wherein said lysosomotropic agent is L-glutamic acid dimethyl ester.

4. The method of claim 1, wherein said lysosomotropic agent is L-leucyl-L-leucine-O-methyl ester.

5. The method of claim 2, which further comprises the step of immortalizing said activated lymphocytes, wherein said step of immortalizing is selected from the group consisting of fusion of activated lymphocytes with human or murine myelomas, infections of said lymphocytes with Epstein-Barr virus, fusion with a lymphoblastoid cell line and fusion with lymphoma cells.

6. The method of claim 3, which further comprises the step of immortalizing said activated lymphocytes, wherein said step of immortalizing is selected from the group consisting of fusion of activated lymphocytes with human or murine myelomas, infections of said lymphocytes with Epstein-Barr virus, fusion with a lymphoblastoid cell line and fusion with lymphoma cells.

7. The method of claim 4, which further comprises the step of immortalizing said activated lymphocytes, wherein said step of immortalizing is selected from the group consisting of fusion of activated lymphocytes with human or murine myelomas, infections of said lymphocytes with Epstein-Barr virus, fusion with a lymphoblastoid cell line and fusion with lymphoma cells.

8. The method of claim 5, which further comprises culturing said immortalized activated lymphocytes and recovering monoclonal antibodies produced by said immortalized activated lymphocytes.

9. The method of claim 6, which further comprises culturing said immortalized activated lymphocytes and recovering monoclonal antibodies produced by said immortalized activated lymphocytes.

10. The method of claim 7, which further comprises culturing said immortalized activated lymphocytes and recovering monoclonal antibodies produced by said immortalized activated lymphocytes.

11. The method of claim 1 wherein said lysosomotropic agent is a peptide having a C-terminal L-leucine-O-methyl ester.

* * * * *

UNITED STATES PATENT AND TRADEMARK OFFICE
CERTIFICATE OF CORRECTION

PATENT NO. : 5,567,610

DATED : October 22, 1996

INVENTOR(S): CARL BORREBAECK ET AL.

It is certified that error appears in the above-identified patent and that said Letters Patent is hereby corrected as shown below:

Title page,
REFERENCES CITED, [56]

Other Publications, "Hoffman et al. in Principle of In Vitro Immunization of Human Blymplocyts, pp. 277-289. Plenun Press 1995 ." should be deleted.
Other Publications, after Borrebaeck, C. A. K. (1986), "Tibtech, 49 147" should read --Tibtech, 4, 147--.

COLUMN 1

Line 5, "continuation-in-part" should read --continuation--.
Line 21, "K" should read Köhler--.
Line 22, "öhler" should be deleted.
Line 37, "extensive extensive" should read --extensive--.
Line 46, "so-called" should read --(so-called--.
Line 52, "ment,i" should read --ment,--

COLUMN 2

Line 30, "int." should be deleted.
Line 31, "al." should be deleted.

COLUMN 3

Line 19, "vital," should read --viral,--
Line 56, "1640with" should read --1640 with--.

UNITED STATES PATENT AND TRADEMARK OFFICE
CERTIFICATE OF CORRECTION

PATENT NO. : 5,567,610

DATED : October 22, 1996

INVENTOR(S) : CARL BORREBAECK ET AL.

It is certified that error appears in the above-identified patent and that said Letters Patent is hereby corrected as shown below:

COLUMN 4

Line 57, "(10 cells/ml)" should read --$10^7$ cells/ml)--.
    Line 67, "M" should read --Möller,--.

COLUMN 5

Line 1, "öller," should be deleted.
    Line 31, "Were" should read --were--.

COLUMN 6

Line 32, "the Table" should read --Table 4--.
    Table 4, "51" should read --5--.

COLUMN 7

Line 7, "malign" should read --a malignant--.
    Line 11, "Stand." should read --Scand.--.
    Line 16, "HF2-conditioned" should read --$HF_2$-conditioned--.
    Line 31, "the" (second occurrence) should be deleted.
    Line 32, "Table" should read --Table 5--.
    Table 5 at line 37, "nised" should read --nized--.
    Table 5 at line 40-41, "Number of speci-fic hybrids*" should read -- Number of speci-fic hybrids#--.

UNITED STATES PATENT AND TRADEMARK OFFICE
CERTIFICATE OF CORRECTION

PATENT NO. : 5,567,610

DATED : October 22, 1996

INVENTOR(S) : CARL BORREBAECK ET AL.

It is certified that error appears in the above-identified patent and that said Letters Patent is hereby corrected as shown below:

<u>COLUMN 8</u>

Line 7, "(1967)" should read --(1967))--.
    Line 10, "Dovine" should read --bovine--.
    Line 12, "the Table" should read --Table 6--.
    Table 6 at line 20, "Number of speci-fic hybrids*" should
       read --Number of speci-fic hybrids#--.
    Line 38, "maligment" should read --malignant--.

<u>COLUMN 9</u>

Line 2, "HYBRODOMAS" should read --HYBRIDOMAS--.
    Line 14, "motrophic" should read --somotrophic--.

Columns 9 and 10, lines 22, 24, 26, and 29, change "lysosomotropic" to --lysosomotrophic--.

Signed and Sealed this

Third Day of June, 1997

*Attest:*

BRUCE LEHMAN

*Attesting Officer*     Commissioner of Patents and Trademarks